United States Patent [19]

Parks

[11] Patent Number: 4,666,433

[45] Date of Patent: May 19, 1987

[54] GASTROSTOMY FEEDING DEVICE

[75] Inventor: Stephen K. Parks, Sunnyvale, Calif.

[73] Assignee: Medical Innovations Corporation, Milpitas, Calif.

[21] Appl. No.: 790,242

[22] Filed: Oct. 22, 1985

Related U.S. Application Data

[63] Continuation-in-part of Ser. No. 670,381, Nov. 5, 1984.

[51] Int. Cl.$^4$ ............................................. A61M 25/00
[52] U.S. Cl. ............................ 604/178; 128/DIG. 12
[58] Field of Search .................. 604/97, 96, 104, 175, 604/174, 178, 180, 280; 188/DIG. 26

[56] References Cited

U.S. PATENT DOCUMENTS

| | | | |
|---|---|---|---|
| 3,149,868 | 8/1964 | Tascalevich | 604/93 |
| 3,253,594 | 5/1966 | Matthews et al. | 604/178 X |
| 3,915,171 | 10/1975 | Shermata | 604/104 X |
| 4,089,337 | 5/1978 | Kronner | 604/178 X |
| 4,114,625 | 9/1978 | Onat | 604/96 |
| 4,392,855 | 7/1983 | Oreopoulos | 604/174 |
| 4,393,873 | 7/1983 | Nawash et al. | 604/174 X |
| 4,516,968 | 5/1985 | Marshall | 604/174 |
| 4,543,089 | 9/1985 | Moss | 604/93 |

OTHER PUBLICATIONS

Moss, "Efficient Gastroduodenal Decompression with Simultaneous Full Enteral Nutrition: A New Gastronomy Catheter Technique", Journal of Parenteral and Enteral Nutrition, vol. 8, No. 2, 3/14/84, pp. 203-207.

Primary Examiner—Stephen C. Pellegrino
Attorney, Agent, or Firm—Willie Krawitz

[57] ABSTRACT

A device is disclosed for supplying food and medication to a patient, and for drainage and/or decompression, the device being inserted through a stoma and into the patient's stomach.

The device is secured in place by an inflatable balloon or a mushroom tip within the stomach, and by an adjustable ring on the abdominal wall. The adjustable ring also prevents ingestion of the device into the stomach. During use, the ring can be retracted to permit cleaning of the stoma area. The ring can be perforated and ribbed to provide improved ventilation of the stoma area during use.

The device can be used with conventional surgically formed procedures, and is replaceable at considerably longer intervals than present devices. Servicing of the device can be made at home, rather than at a hospital.

8 Claims, 5 Drawing Figures

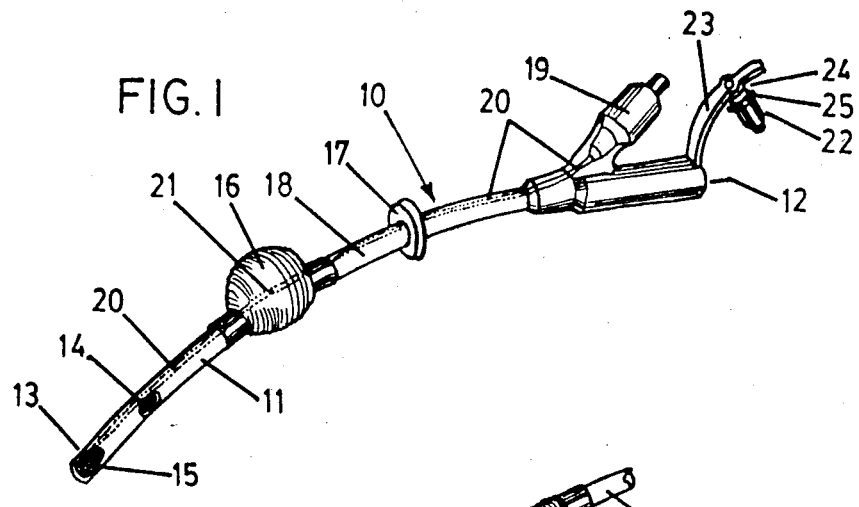
FIG. 1
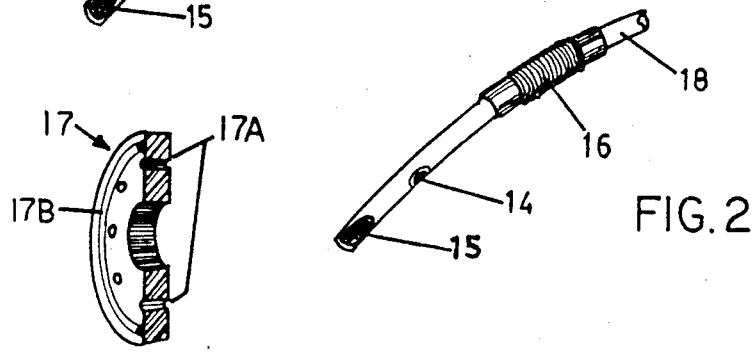
FIG. 4
FIG. 2
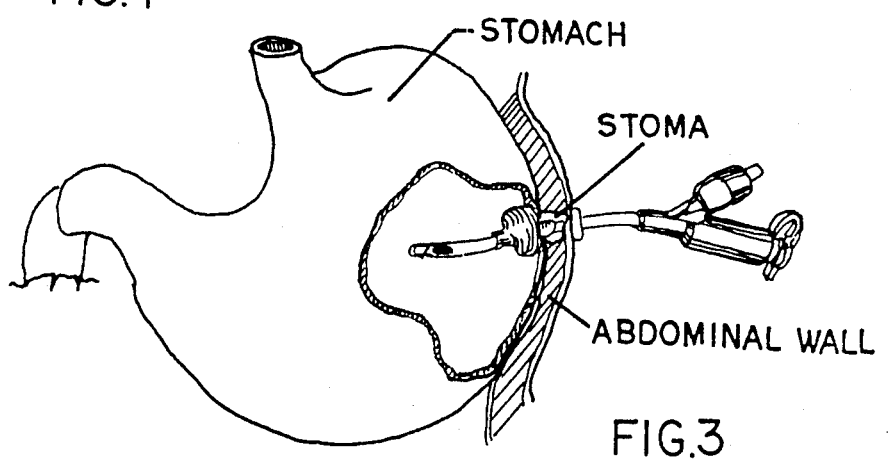
FIG. 3

GASTROSTOMY FEEDING DEVICE

BACKGROUND OF THE INVENTION

The application is a continuation-in-part of U.S. Ser. No.: 670,381, filed on Nov. 5, 1984.

The invention relates to a new and improved feeding tube, nad more specifically to a gastrostomy feeding tube that is insertable through a stoma in the patient's stomach wall and secured within the patient's stomach and against the abdominal wall.

Many types of feeding devices have been developed, but they suffer from various drawbacks. These include: the ejection or loss of liquids from the stomach and back out through the device; leaking around the periphery of the device; and, premature deterioration of the materials of construction. Also, it is difficult to maintain the device in place in a stable manner in the patient, and this latter problem can result in the device being ingested into the stomach, and eventually into the pylorum. Devices presently on the market are not sized properly, and they use materials that are prone to fairly rapid deterioration. Moreover, they can become entangled and dislodged from the patient due to improper sizing and inadequate locking of the device to the patient. In some prior art devices, the exterior of the gastrostomy tube is taped to the wearer's body, and this can cause infection at the stoma entry, and along the taped area, as well as causing irritation due to the difficulty in maintaining these areas clean.

Other prior art devices employ a spring biased or threaded locking mechanism to secure a locking ring to the wearer's body, the locking ring being fastened on the gastrostomy tube. But these devices maintain a fixed pressure or position of the locking ring on the gastrostomy tube, and do not self adjust to peristaltic pressure of the stomach. This is of particular importance in the case of neonatal patients or other types of patients (e.g., incoherent or unconscious) who are unable to communicate the nature of their discomfort. Generally, the use of tape or mechanical locking devices requires extra care which is usually provided by trained personnel such as nurses.

THE INVENTION

According to the invention, a gastrostomy feeding tube is provided for insertion thorough the stoma of the patient's stomach wall and into the patient's stomach. The gastrostomy tube has an inflatable balloon at its inner end to position and secure the tube within the stomach and to function as a gasket. The outer end of the tube has a moveable locking ring that can be adjusted by frictional engagement of the locking ring with the gastrostomy tube to accommodate to the size of the wearer.

Since the locking ring does not require or use tape to secure the device in place, problems associated with skin irritation and with maintaining both the taped areas and the stoma area clean, are greatly reduced. The locking ring can be easily retracted along the tube against the frictional force between the ring and the tube to permit cleaning of the stoma entry through which the catheter is inserted. The locking ring is then repositioned to its normal location, i.e., in close contact with the wearer's abdomen.

The balloon and locking ring thus both function to maintain the device in place, and prevent the device, by frictional engagement between the locking ring and tube, from being drawn into the stomach, or being inadvertently pulled out. If desired, a mushroom tip can be used in place of a balloon, and this can be important during the first few post operative days when a balloon tip is more vulnerable to being ruptured.

The device of this invention is preferably manufactured of a medical grade silicone elastomer, rather than a latex or silicone latex combination. Consequently, use of the silicone elastomer provides a relatively inert material compared to the latex. Use of a silicone elastomer enables replacement of the device about every 6-8 weeks compared to a device employing a silicone latex which needs replacement about every 3 weeks.

BRIEF DESCRIPTION OF THE DRAWINGS

FIG. 1 is an external perspective view of the gastrostomy device of this invention;

FIG. 2 is an external perspective view of the said device, fragmented, showing the outlet end, and the balloon when deflated;

FIG. 3 is a perspective view, partly broken away, of the said device installed in a patient;

FIG. 4 is an external perspective view of a preferred form of locking ring employed in the device; and, FIG. 5 is an external perspective view showing the use of a mushroom tip in place of the balloon, together with a perforated and ribbed locking ring.

DESCRIPTION OF THE PREFERRED EMBODIMENTS

Figure 5:
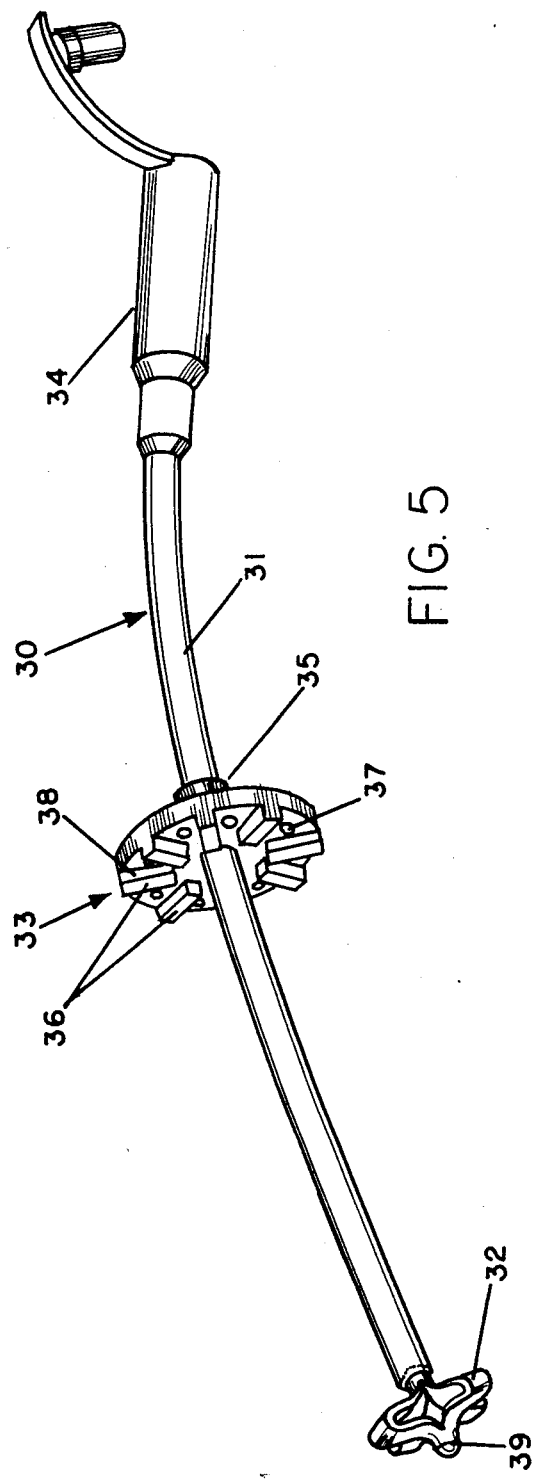

The gastrostomy catheter device 10 of this invention is shown in FIG. 1, and provides an inlet end 12, through which is fed food and medication, and an outlet end 13, that extends into the patient's stomach. The inlet and outlet ends can also be employed for drainage and/or decompression. A plurality of outlet ports, two of which ports 14, 15 are shown, and are located at the outlet end 13. The catheter 10 is secured inside the stomach by an inflatable balloon 16, and on the patient's abdomen by an adjustable silicone locking ring 17. As shown in FIG. 4, the locking ring 17 is provided with a plurality of vent holes 17A and a circular ridge 17B to permit air to contact the entry to the stoma and reduce infection and skin irritation.

As indicated, use of the ring prevents the catheter from being drawn into the patient's stomach. In addition, since the adjustable ring does not require the use of tape, a potential source of skin irritation and infection is eliminated. The portion 18 of the catheter tube 11 between the ring 17 and balloon 16 is secured within the stoma, and this arrangement of the balloon and ring prevents the catheter from being drawn into the patient's stomach.

In FIG. 1, the balloon is inflated by liquid or gas which is passed through a valve 19 and line 20 into a port 21 that is surrounded by the balloon. The line 20 is bonded along the inside of the catheter tube 11 and extends to the outlet of the catheter where it is end sealed; the end seal forces the inflating gas into the port 21. FIG. 2 shows the balloon 16 in a deflated position.

The inlet end 12 is provided with an integrally formed end plug 22 attached to the catheter by a band 23. A plurality of rings 24, 25 are formed on the plug to engage corresponding grooves (not shown) on the inside of the bore at the inlet. The combined effect of the plug and bore fit, and the fit between the grooves and rings prevent the plug from being dislodged during use, and hence, will prevent the contents of the stomach from draining out the catheter.

Basically, the catheter device is inserted into the patient through a surgically prepared stoma created in the abdominal wall using pre-existing surgical procedures. These procedures include Stamms Gastrostomy, Witzel Gastrostomy, and other. Also, non surgical procedures may be employed such as percutaneous gastrostomy. The Janeway surgical procedure also may be employed. The catheter tube 10, with surrounding concentric purse string sutures, is inserted through the stoma and gastric wall into the stomach. The purse strings will permanently invaginate a portion of the stomach and stoma to shape around the catheter tube and then will dissolve, leaving the gastrostromy tube in place and ready for use. FIG. 3 shows the device when installed. The inflated balloon forms a gasket that seals the entrance to the stoma, and along with the locking ring 17, secures the device in place. The device may be constructed in various sizes to accommodate a particular patient. Sizes such as 12, 14, 16, 18 and 20 French, and corresponding diameters varying from about 0.157"-0.263", and a wall thickness of about 0.035", may be used.

After being used for a suitable time, say 6–9 weeks, the catheter tube is, of course, replaced. This is accomplished simply by deflating the balloon, retracting the adjustable ring, and removing the tube from the patient.

FIG. 5 illustrates the use of a mushroom tip emplyed in place of a balloon, and a locking ring designed to provide air circulation between the ring and stoma area to reduce irritation and the possibility of infection. The gastrostomy catheter device 30 includes a tube portion 31, mushroom tip 32, adjustable locking ring 33, and food inlet portion 34. The locking ring 33 includes a collar 35 and a plurality of raised, concentric legs 36, air vents 37, and air gaps 38 between the legs 36 to permit circulation of air between the ring and stoma area. The mushroom tip 32 is inserted (and removed) with a stylet through the tube and expands to its final shape in the stomach when it is pushed through the tube. The food inlet 34 has the same construction as that shown in FIG. 1.

It will be appreciated that while a balloon or mushroom tip are disclosed as being the preferred embodiments for securing the device internally, components such as a plate may be used as a substitute for the balloon or mushroom tip components.

The operation of the locking ring 33 is the same as that of the ring 17 in FIG. 1. Basically, the locking ring 33 is adjustable along the tube 31 and forms a light friction lock against the user's abdomen. When the stoma area requires cleaning, the ring 33 is simply retracted against the frictional force between the ring and tube 31, and then forced back against the abdomen after the stoma area has been cleaned. Usually, the locking ring 33 and tube 31 are both made of medical grade silicone material.

The present device is inexpensive and can be readily manufactured by conventional extrusion and injection molding techniques. Also, it can be easily inserted for use without generally requiring the services of a physician or even outpatient services. Furthermore, when in a hospital, nursing times with its attendant costs have been found to be reduced significantly.

The device may be cleaned during use and can be manipulated to permit cleaning of the stoma area. Finally, the device is safe in that it cannot be drawn into the stomach, which can be particularly dangerous to unsuspecting patients such as infants, and incoherent and unconscious individuals. During use, it will not inadvertantly drain the contents of the stomach, because of the end plug.

I claim:
1. A gastrostomy catheter device for feeding into a patient's stomach, comprising:
   a. an elongate feeding tube, including an outer extension from the patient's stomach, the tube having a feeding inlet end mounted on the outer extension and an outlet end positioned within the patient's stomach;
   b. an expandable mushroom tip positioned at the outlet end of the tube;
   c. a closure plug for the feeding inlet and secured to the feeding tube by an integral band; and,
   d. a locking ring positioned medially along the outer extension of the tube, and sized to frictionally engage the tube, and slidably mounted therealong, and adjustable solely by frictional engagement with the tube to accommodate to the size of the wearer, the locking ring providing a plurality of perforations and spaced ridges to enable air circulation between the locking ring and patient's body; whereby,
   i. when the mushroom tip is contracted, the feeding tube may be inserted through a stoma and into the patient's stomach;
   ii. when the mushroom tip is expanded, it will secure the device within the patient's stomach and form a seal adjacent the stoma;
   iii. securement of the ring to the tube being provided solely by frictional engagement therebetween, to secure the device within the patient's body and to prevent undesirable movement of the ring along the tube, whether in the dry state or when lubricated by body fluids, the locking ring being manually adjustable along the tube to accommodate to the size of the patient, and the mushroom tip and ring both functioning to maintain the device in place in the patient;
   iv. retraction of the ring being entirely against the force of frictional engagement to enable the stoma and adjacent areas to be cleaned; and,
   v. when the mushroom tip is contracted, retraction of the ring enables the device to be removed from the patient.

2. The catheter of claim 1, constructed of a medical grade silicone elastomer, and the like.

3. The catheter of claim 2, in which the spaced ridges of the locking ring are arranged concentrically of the ring.

4. The catheter device of claim 1, in which the locking ring defines spaced ridges directed radially outwards from the ring.

5. A method for gastrostomy feeding, comprising:
   a. inserting a gastrostomy tube though a stoma and into a patient's stomach; and,
   b. supplying food through the tube to the patient's stomach, the said tube comprising:
   1. an elongate feeding tube, including an outer extension from the patient's stomach, the tube having a feeding inlet end mounted on the outer extension and an outlet end positioned within the patient's stomach;
   2. an expandable mushroom tip positioned at the outlet end of the tube;

3. a closure plug for the feeding inlet and secured to the feeding tube by an integral band; and,
4. a locking ring positioned medially along the outer extension of the tube, and sized to frictionally engage the tube, and slidably mounted therealong, and adjustable solely by frictional engagement with the tube to accommodate to the size of the wearer, the locking ring providing a plurality of perforations and spaced ridges to enable air circulation between the locking ring and patient's body; whereby,
  i. when the mushroom tip is contracted, the feeding tube may be inserted through a stoma and into the patient's stomach;
  ii. when the mushroom tip is expanded, it will secure the device within the patient's stomach and form a seal adjacent the stoma;
  iii. securement of the ring to the tube being provided solely by frictional engagement therebetween, to secure the device within the patient's body and to prevent undesirable movement of the ring along the tube, whether in the dry state or when lubricated by body fluids, the locking ring being manually adjustable along the tube to accommodate to the size of the patient, and the mushroom tip and ring both functioning to maintain the device in place in the patient;
  iv. retraction of the ring being entirely against the force of frictional engagement to enable the stoma and adjacent areas to be cleaned; and,
  v. when the mushroom tip is contracted, retraction of the ring enables the device to tbe removed from the patient.

6. The method of claim 5, in which the tube and locking ring are constructed of a medical grade silicon elastomer, and the like.

7. The method of claim 5, in which the spaced ridges of the locking ring are arranged concentrically of the ring.

8. The method of claim 5, in which the locking ring defines spaced ridges directed radially outwards from the ring.

* * * * *